(12) United States Patent
Chang et al.

(10) Patent No.: US 11,172,867 B2
(45) Date of Patent: Nov. 16, 2021

(54) PHYSIOLOGICAL INFORMATION RECORDING DEVICE AND PHYSIOLOGICAL INFORMATION RECORDING METHOD THEREOF

(71) Applicant: Chang Gung University, Taoyuan (TW)

(72) Inventors: Ya-Ju Chang, Taoyuan (TW); Jiunn-Woei Liaw, Taoyuan (TW)

(73) Assignee: CHANG GUNG UNIVERSITY, Taoyuan (TW)

( * ) Notice: Subject to any disclaimer, the term of this patent is extended or adjusted under 35 U.S.C. 154(b) by 171 days.

(21) Appl. No.: 16/558,751

(22) Filed: Sep. 3, 2019

(65) Prior Publication Data
US 2020/0069234 A1     Mar. 5, 2020

(30) Foreign Application Priority Data

Sep. 5, 2018 (TW) .................................. 107131149

(51) Int. Cl.
| | | |
|---|---|---|
| *A61B 5/00* | (2006.01) | |
| *A61B 5/103* | (2006.01) | |
| *A61B 5/11* | (2006.01) | |
| *A61B 5/107* | (2006.01) | |

(52) U.S. Cl.
CPC .......... *A61B 5/4023* (2013.01); *A61B 5/1036* (2013.01); *A61B 5/1074* (2013.01); *A61B 5/1077* (2013.01); *A61B 5/1116* (2013.01); *A61B 2562/0247* (2013.01); *A61B 2562/046* (2013.01)

(58) Field of Classification Search
CPC ... A61B 5/4023; A61B 5/1036; A61B 5/1074; A61B 5/1077; A61B 5/1116; A61B 2562/0247; A61B 2562/046; G01G 19/44; G01G 19/50
See application file for complete search history.

(56) References Cited

U.S. PATENT DOCUMENTS

| | | | | |
|---|---|---|---|---|
| 8,131,498 B1 * | 3/2012 | McCauley | ........... | A63B 26/003 |
| | | | | 702/139 |
| 8,475,367 B1 * | 7/2013 | Yuen | .................. | A61B 5/02007 |
| | | | | 600/300 |
| 9,526,946 B1 * | 12/2016 | Zets | ..................... | A61B 5/6892 |
| 2004/0000195 A1 | 1/2004 | Yanai et al. | | |

(Continued)

FOREIGN PATENT DOCUMENTS

| | | |
|---|---|---|
| CN | 1969741 A | 5/2007 |
| CN | 103356203 A | 10/2013 |
| TW | 201618019 A | 5/2016 |

*Primary Examiner* — Devin B Henson
(74) *Attorney, Agent, or Firm* — Li & Cai Intellectual Property (USA) Office

(57) ABSTRACT

A device for recording physiological information includes a carrier board comprising a plurality of force transducers and a plurality of contact sensing elements; and a processing unit, coupled to the force transducers and the contact sensing elements, configured to determine a center of gravity (COG) according to outputs of the force transducers, configured to determine a contacted range according to outputs of the plurality of contact sensing elements, configured to record the center of gravity and the contacted range, wherein the gravity and the contacted range substantially correspond to the same time point.

19 Claims, 10 Drawing Sheets

(56) References Cited

U.S. PATENT DOCUMENTS

| | | | |
|---|---|---|---|
| 2007/0027369 A1* | 2/2007 | Pagnacco | A61B 5/1071 |
| | | | 600/301 |
| 2013/0289889 A1 | 10/2013 | Yuen et al. | |
| 2014/0131120 A1 | 5/2014 | Horst et al. | |
| 2014/0180172 A1* | 6/2014 | Uchiyama | A61B 5/1116 |
| | | | 600/595 |
| 2016/0007903 A1* | 1/2016 | Lonis | A61B 5/6892 |
| | | | 600/595 |
| 2017/0258388 A1* | 9/2017 | Gomez del Campo | |
| | | | A61B 5/1036 |

\* cited by examiner

PHYSIOLOGICAL INFORMATION RECORDING DEVICE AND PHYSIOLOGICAL INFORMATION RECORDING METHOD THEREOF

CROSS-REFERENCE TO RELATED PATENT APPLICATION

This application claims the benefit of priority to Taiwan Patent Application No. 107131149, filed on Sep. 5, 2018. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a physiological information recording device, and more particularly to a physiological information recording device capable of performing a more comprehensive balance assessment of a user according to a center of gravity and an actually contacting surface.

BACKGROUND OF THE DISCLOSURE

An existing balance board design mainly disposes the force transducer in a plurality of positions (for example, four corners) to obtain a user's center of gravity (COG) projected onto the balance board and to detect a user's center of gravity offset, for judging a user's balance ability. However, in practical applications, the control that users have on their center of gravity depends largely on factors such as whether they are standing with their feet apart or together. Therefore, under the existing balance board design, only a center of gravity (COG) offset is not enough to accurately evaluate the user's balance ability. For the above reasons, although the existing balance board design may be used for entertainment, its purpose for research or medical rehabilitation is slightly insufficient, and even for the original purpose of entertainment, there is a problem that the operation is not accurate enough.

Even if two balance board splicing methods are used, each balance board performs its own functions and separately detects the left and right feet of the user, so as to improve pertinence and precision of the test, and try to make up for the aforementioned shortcomings of the existing balance board. However, these practices will increase the cost, and if the users stand with their feet too close together, accuracy of the measurement result can easily be lowered due to an edge of the two balance boards being too close, so that the original purpose of improving the accuracy cannot be achieved. In addition, adopting a two balanced board splicing method also has problems in signal processing time synchronization.

On the other hand, there is another sensing pad for research or medical rehabilitation purposes, which detects the pressure value received at each point by setting a large number of pressure sensing elements to collect each measured point to obtain a center of pressure (COP). Pressure values received by each point are separately detected to collect data of each measured point, and a large amount of data is processed by floating point operation. However, under these settings, the pressure sensing elements used at each point must be able to cover a wide range of pressure value detection in order to detect the signal at each point that is touched, and the signal of the pressure at the single point when under full weight, and even detect a pressure signal generated by the single point of 1.5 or even 2 times the weight. Therefore, specifications (e.g., resolution and accuracy) of the pressure sensing element are very high, which imposes a great burden on the cost. On the other hand, in order to meet accuracy requirements of practical applications, layout density requirements for pressure sensing elements are also very high. At the same time, in order to improve the speed of message collection to cope with the large amount of floating-point computing data at any given time, it is necessary to set up more high resolution (e.g., 10 bits) analog-to-digital converters (ADCs) to process messages, so that a very large number of pressure sensing elements and ADCs must be used. As can be seen from the above various conditions, the cost of such sensing pads is very high. On the other hand, since any inductive component or ADC failure will affect the overall judgment error. Each sensing component and ADC must have errors between components. Therefore, in order to improve accuracy, it is necessary to calibrate each component before use. The pressure sensing element must also be calibrated frequently in the maintenance of the sensing pad, which also imposes a considerable burden on the labor cost. Moreover, the COG is substantially the same as the COP only when the user is standing still; the COG is significantly different from the COP as the user moves. That is to say, COP cannot be completely equated with the center of gravity (COG). In other words, the use of the center of pressure (COP) as a measure of balance is not as good as the use of the center of gravity (COG) as an assessment of balance. In addition to the aforementioned problems, although the sensing pads used in these studies can provide relatively accurate detection data for each point of force, however, it is difficult to obtain the total weight of the load on it, so that some shortcomings are still present in the application thereof.

Therefore, the existing technology still has room for improvements, and it is necessary to propose a device capable of achieving a purpose of multi-function detection at low cost, and intelligently providing further services such as automatic identification, judgment, recording and recommendation in addition to various basic measurement functions.

SUMMARY OF THE DISCLOSURE

The disclosure provides a device for recording physiological information. The device comprises: a carrier board comprising a plurality of force conductors and a plurality of contact sensing elements; and a processing unit, coupled to the force transducers and the contact sensing elements, configured to determine a center of gravity (COG) according to outputs of the force transducers, configured to determine a contacted range according to outputs of the plurality of contact sensing elements, configured to record the center of gravity (COG) and the contacted range, wherein the center of gravity and the contacted range substantially correspond to the same time point.

The disclosure provides a method applied to a physiological information recording device that includes a carrier board comprising a plurality of force transducers and a plurality of contact sensing elements, and a processing unit. The method comprises: receiving outputs of the force transducers and outputs of the contact sensing elements; determining, by the processing unit, a gravity and a center of gravity according to the outputs of the force transducers; determining, by the processing unit, a contacted range according to the outputs of the contact sensing elements; and recording, by the processing unit, the center of gravity and the contacted range, wherein the center of gravity and the contacted range substantially correspond to the same time point.

It is to be understood that both the foregoing general description and the following detailed description are described by examples, and are intended to provide further explanation of the disclosure as claimed.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
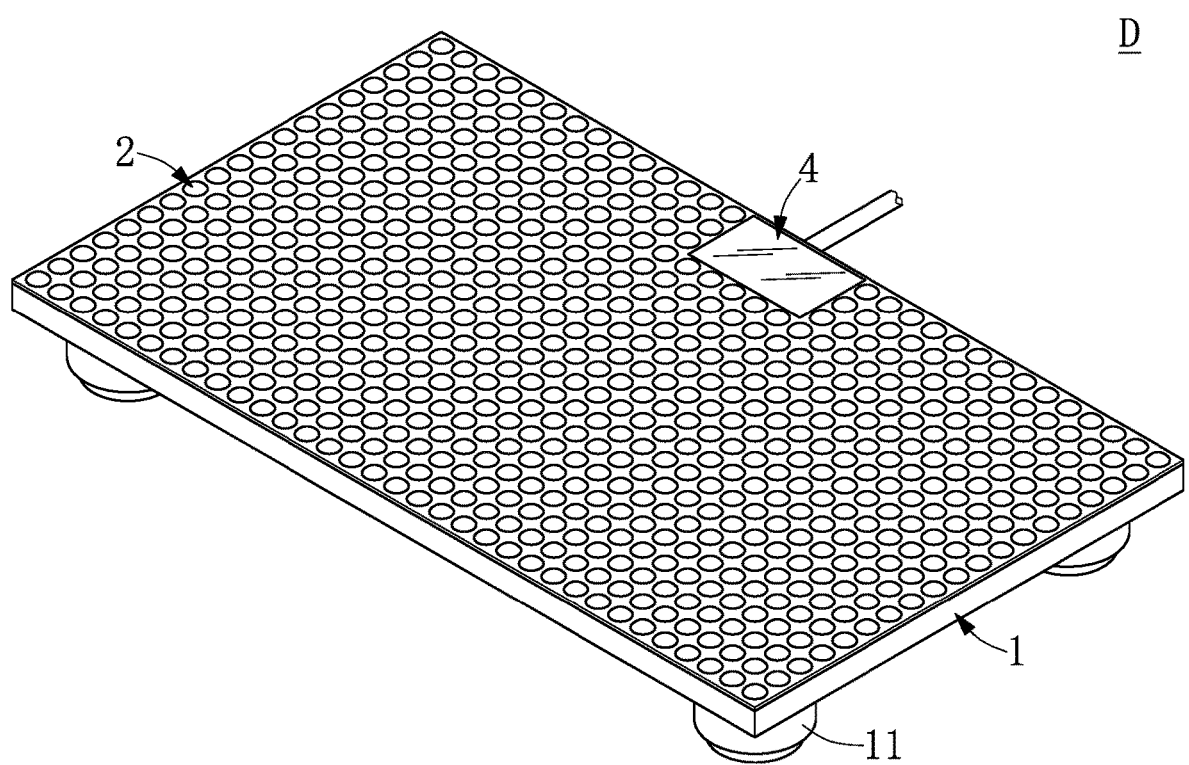
FIG. 1 is a perspective schematic view of a physiological information recording device according to a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Figure 2:
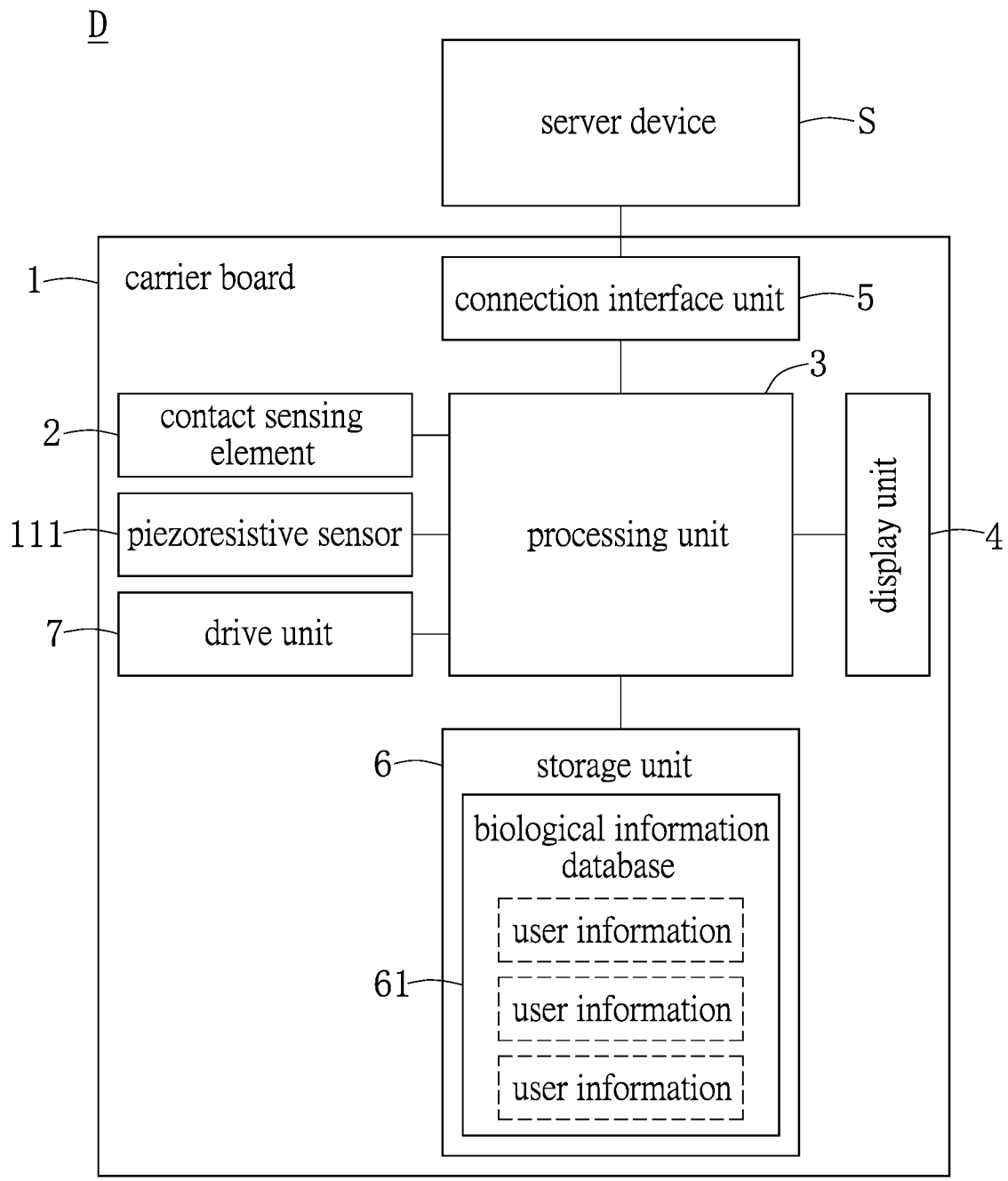
FIG. 2 is a block diagram of the physiological information recording device according to the first embodiment of the present disclosure.

Referring to FIG. 1 and FIG. 2, FIG. 1 is a perspective schematic view of a physiological information recording device according to a first embodiment of the present disclosure, and FIG. 2 is a block diagram of the physiological information recording device according to the first embodiment of the present disclosure. As can be seen from the above FIG.s, the present disclosure provides a physiological information recording device D including a carrier board 1 and a plurality of contact sensing elements 2 disposed on the surface of the carrier board 1. In this embodiment, a bottom surface of four corners of the carrier board 1 is respectively provided with a supporting foot 11, and each supporting foot 11 is respectively provided with a force transducers 111. When the user stands on the carrier board 1, each force transducer 111 generates a signal. Specifically, the four corners of the force transducer 111 can define a plane (at least three force transducers 111 can define the plane), and according to a force applied to the plane, and a distance between a force-bearing point and each of the force transducers 111 (that is, torque), each force transducer 111 receives the corresponding force value. Therefore, according to the signal sent by each of the force transducer 111, a position and size of the force-bearing point can be calculated. It should be noted that in the present embodiment, although the force transducer 111 is disposed in the supporting foot 11 on the bottom surface of the carrier board 1, the present disclosure is not limited thereto. As long as the force transducers 111 can define at least one plane and can record the force applied to the carrier board 1 by appropriate arrangement, the spirit of the present disclosure can be met, and the details of other specific structures are not limited to the present disclosure.

Referring to FIG. 1 and FIG. 2, in the present embodiment, the physiological information recording device D further includes a processing unit 3, a display unit 4, a connection interface unit 5, a storage unit 6 and a drive unit 7. The force transducers 111, the contact sensing element 2, the display unit 4, the connection interface unit 5, the storage unit 6, and the drive unit 7 are all coupled to the processing unit 3. The processing unit 3 may be a central processing unit (CPU), micro-controller, or a graphics processing unit (GPU), and the like, but is not limited thereto. The processing unit 3 can receive output signals from the force transducers 111 and the contact sensing element 2, and perform subsequent synchronically analysis operations. In this embodiment, the carrier board 1 includes the contact sensing components 2 and the force transducers 111. Therefore, when the user stands on the carrier board 1, the contact sensing components 2 and the force transducers 111 simultaneously generate corresponding output signals to the processing unit 3, wherein the output signals of the contact sensing components 2 and the force transducers 111 correspond to the same time point. The processing unit 3 simultaneously records the output signals of the contact sensing components 2 and the force transducers 111. The processing unit 3 synchronous analyzes the output signals of the sensing component 2 and the force transducers 111 to produce an analysis result. Through this analysis result, intelligent identification, judgment, and recommended services can be achieved. In addition, in order to facilitate the user to obtain the analysis result, the processing unit 3 can drive the display unit 4 to display information for the user to view, or send the signal to a servo device S through the connection interface unit 5, so that the server device S can display more complete and detailed information content.

As described above, in particular, the display unit 4 of the present embodiment may be a display panel (as shown in FIG. 1) disposed on a specific block surface of the carrier board 1 for presenting simple data information on the panel. Thus, when the user stands on the carrier board 1, the basic information required can be obtained by simply looking down the panel, like general scale, which is intuitive and living, and the physiological information recording device D of the present disclosure can be generally popularized. However, the installation position is not limited to the upper surface of the carrier board 1, and may be a separate display protruding from the side of the carrier board 1, or a display device connected to the processing unit 3 by wire or wirelessly.

On the other hand, information presentation manner of the physiological information recording device D of the present disclosure may be sending information to the servo device S by wired (as shown in FIG. 1) or wirelessly. In this way, the information can be further processed in the servo device S, and then the display device carried by the servo device S itself can present more complete and even more visual information in a statistical chart or the like. In a wired connection application mode, the connection interface unit 5 may be a universal serial bus (USB) port for connecting cables, IEEE 1394 port (also known as FireWire interface), Display Port or other ports; in a wireless connection application mode, it can also be a wireless signal transmission module such as Bluetooth, infrared, ZigBee or ANT. The servo device S may be a personal computer or other specialized instrument device with a display when actually applied. The servo device S may be a personal computer or other specialized instrument device with a display when actually applied. Therefore, the user information collected by the physiological information recording device D can be processed into a more professional statistical chart, which is advantageous for the physiological information recording device D of the present disclosure to be applied for more specialized research or medical rehabilitation.

Figure 3:
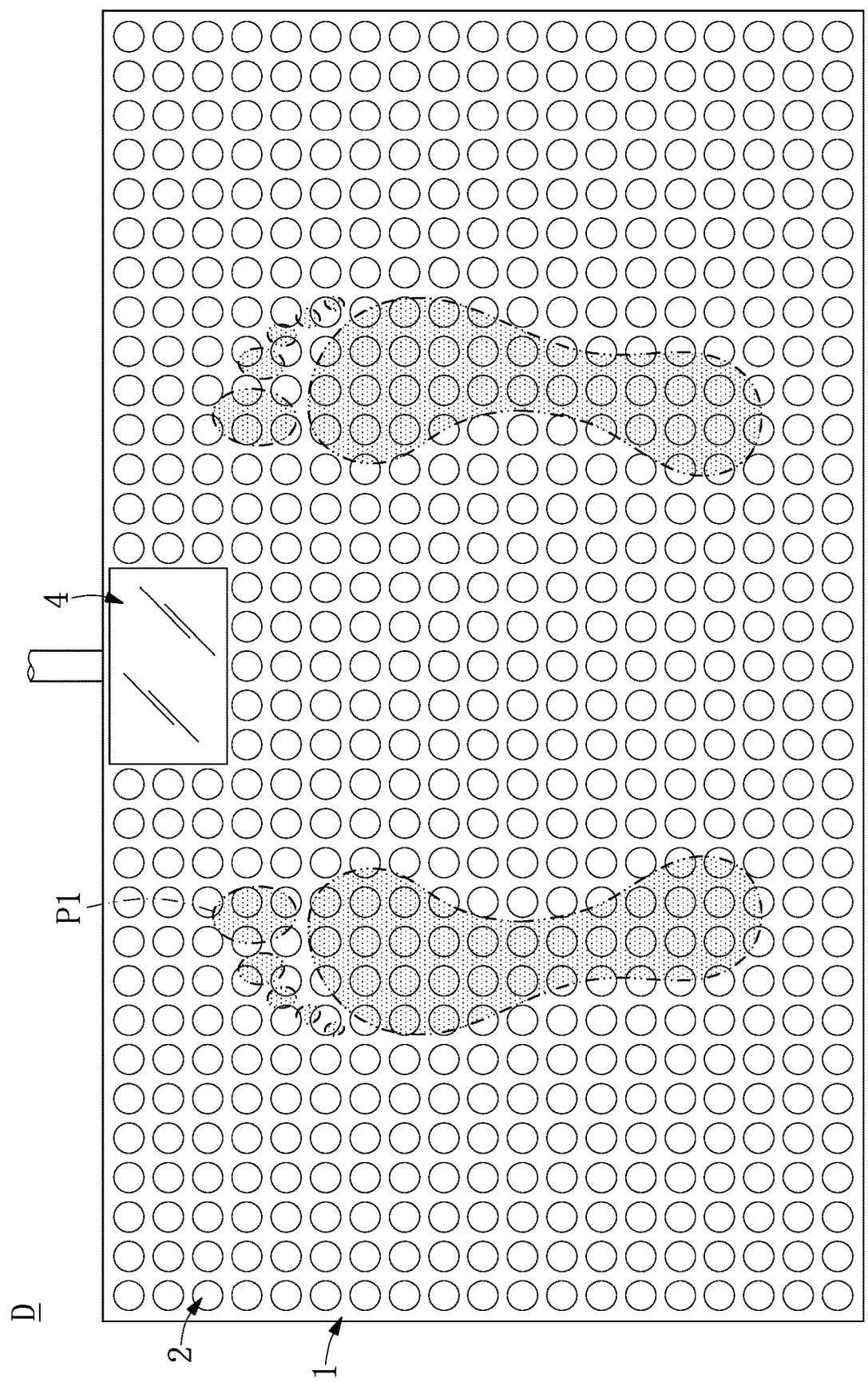
FIG. 3 is a schematic view of a foot contact area of the user's feet standing on the physiological information recording device according to the first embodiment of the present disclosure.
Figure 4:
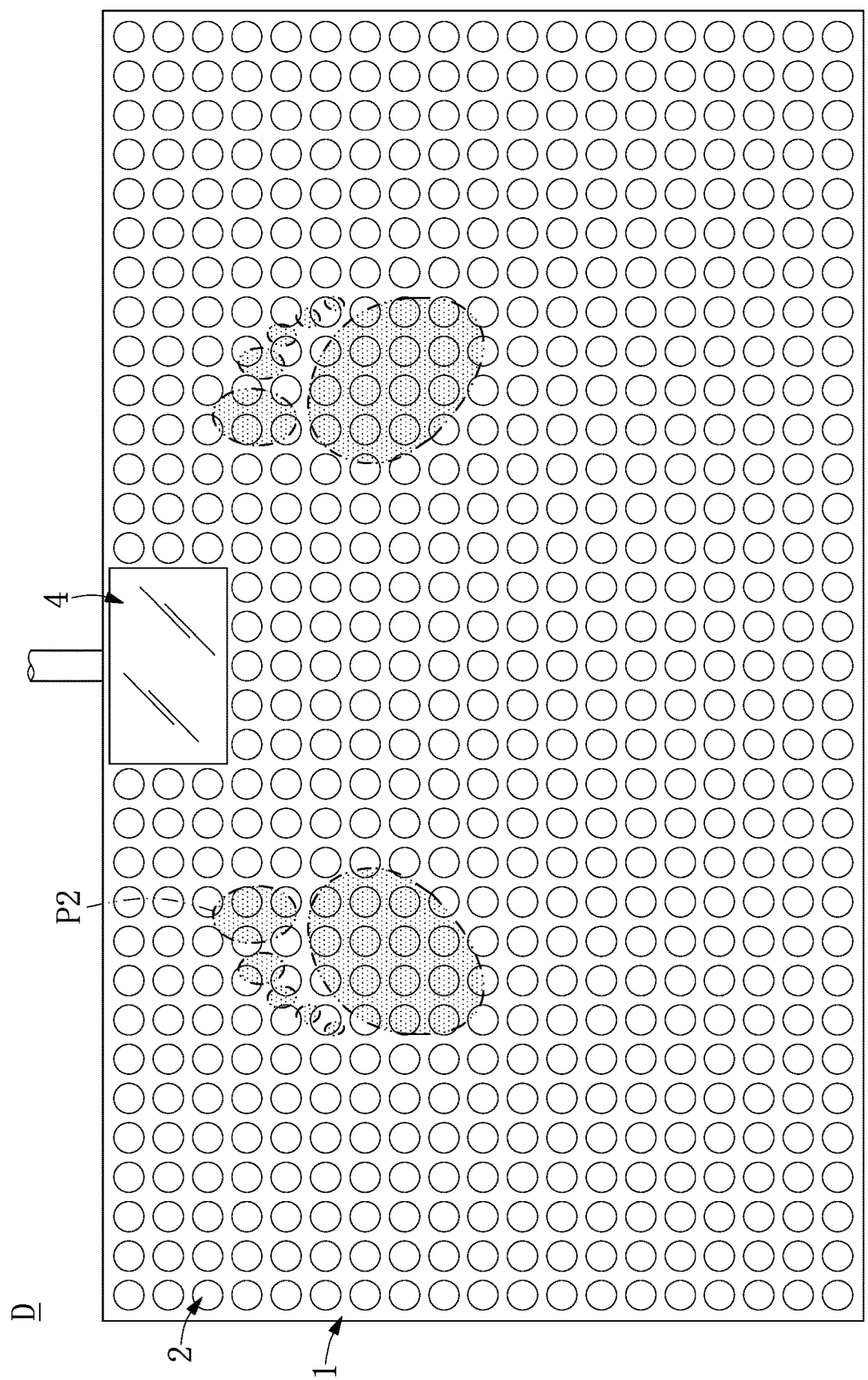
FIG. 4 is a schematic view of a foot contact area of the user's feet standing on tiptoe on the physiological information recording device according to the first embodiment of the present disclosure.

Next, referring to the respective component symbols shown in FIG. 1 and FIG. 2, and refer to FIG. 3 and FIG. 4 together, FIG. 3 is a schematic view of a foot contact area of the user's feet standing on the physiological information recording device according to the first embodiment of the present disclosure, and FIG. 4 is a schematic view of a foot contact area of the user's feet standing on tiptoe on the physiological information recording device according to the first embodiment of the present disclosure. When the user stands on the carrier board 1 with a general standing posture (as shown in FIG. 3), the contact sensing element 2 disposed on the surface of the carrier board 1 is in contact with a user's foot in the foot contact area P1 corresponding to the surface of the user's foot and the carrier board 1, and the signal is received by the processing unit 3. On the other hand, when the user stands on the toe board on the carrier board 1 (as shown in FIG. 4), a foot contact area P2 of the user's foot and the surface of the carrier board 1 becomes smaller (relative to the foot contact area P1 described above), and only the contact sensing element 2 corresponding to the forefoot and toe is contacted to emit a signal.

As can be seen from the above FIG.s, since the physiological information recording device D of the present disclosure has the plurality of contact sensing elements 2 disposed on the surface of the carrier board 1, it is possible to accurately detect the position and area of the contact between the user's foot and the carrier board 1, instead of inversely calculating a force-bearing point abstracted for the entire carrier board 1 according to only the signal received by the force transducers 111. In other words, the processing unit 3 can determine the position and shape of the actual contact between the user U and the surface on the carrier board 1 according to the signals sent by the plurality of contact sensing elements 2. Therefore, according to the information detected by the contact sensing element 2, a manner in which the user stands can be easily known, so that accurate measurement results can be obtained. The user can be standing with their feet together or separate, standing on one foot or on both feet, and standing on toes and other standing posture. In addition, since the processing unit 3 can also calculate the weight of the user U and the center of gravity (COG) position of the user U according to the signal sent by the force transducers 111, the processing unit 3 can also combine the information detected by the force transducers 111 to determine the user's weight and the center of gravity offset. In an embodiment, the processing unit 3 also obtains a COP signal according to the output signals from the contact sensing element 2, and the processing unit 3 performs a correlation analysis between the COG and the COP.

As described above, in the actual application, the contact sensing element 2 can be a low accuracy/resolution element, for example, a membrane switch or a force sensing resistor (FSR for short), That is to say, the contact sensing component 2 can be a low-resolution (such as 1-bit, 2-bit, 4-bit, . . . up to 8-bit) sensing component, Therefore, a more comprehensive interpretation result can be achieved at a very low cost compared to a research device of similar function. It is worth mentioning that, since the present disclosure assists in collecting the user's standing posture related information through a large number of contact sensing elements 2 disposed on the surface of the carrier board 1, there is no need to worry about a bias of the weight or the center of gravity due to a difference in standing posture. Accordingly, a conventional weight meter and the like often mark two footprints, so that the user can only use the specified direction or the standing posture. The physiological information recording device D of the present disclosure can intelligently and automatically determine the standing posture of the user, and the use of the physiological information recording device D in any direction without any influence posture will not affect the correctness of the measurement. Therefore, the convenience in use can be greatly improved.

Referring to FIG. 1 to FIG. 4, in a study of partial physical ability measurement (e.g., Physical fitness, Lower extremity muscle strength test), or in rehabilitation training, an examiner or a therapist will ask a subject or a patient to repeatedly perform an operation of lifting toes and then lowering according to a preset number of times, depending on whether the number of times or the number of groups can be completed to evaluate the physical ability or the rehabilitation result. Since the processing unit 3 of the present disclosure can obtain the number of times of tiptoe of the user U according to the gravity force change of the carrier board 1 and the shape change of the actual contact of the surface on the carrier board 1, the physiological information recording device D of the present disclosure is particularly helpful in the aforementioned application. Specifically, the physiological information recording device D of the present disclosure records the change in a contact area between the user's foot and the surface of the carrier board 1 through the contact sensing element 2, and combines the gravity force change information detected by the force transducers 111, so that after the processing unit 3 receives the same information, it can accurately estimate a number of cycles in which the toes are correctly lifted and then lowered. The processing unit 3 can also accurately record a user's abnormal movement pattern at the first few times, and can continue for several cycles from the beginning of the action to the non-standard action by analyzing the above information, and these information is a very important reference for the evaluation of many physical abilities such as endurance and coordination.

Referring to FIG. 1 and FIG. 2, in the physiological information recording device D of the present embodiment, the storage unit 6 stores a biological information database 61, and the processing unit 3 can read the biological information database 61 or write the information into the biological information database 61. Specifically, the physiological information recording device D of the present disclosure can be used by a plurality of users in practical applications, and can intelligently and automatically record information corresponding to individual users.

More specifically, the processing unit 3 of the present embodiment can determine whether there is a user information corresponding to the user in the biological information database 61 according to the weight of the user and/or the shape of the user actually contacting the surface of the carrier board 1 (including the contour of the foot and even the height of the foot arch) and/or one of the mentioned values in the application. In the case of a new physiological information recording device D, after a first user stands on the carrier board 1, the processing unit 3 determines that there is no corresponding user information in the biological information database 61, therefore, the processing unit 3 establishes user information corresponding to the user in the biological information database 61 according to a weight of the user and a shape of a user's sole actually contacting the surface of the carrier board 1. Then, when the same user uses the same physiological information recording device D again, the processing unit 3 can determine which user is using the physiological information recording device D according to the user information recorded in the biological information database 61. This feature is beneficial for family members to share or for similar applications. In the society of modern small families, the number of members in a family is not very large, and each person's weight, and shape of the foot (e.g., contour of the foot and the height of the arch), may be different, so it is easy to record and discriminate each person's information, and it is also possible to automatically record the period of each test and the results of the test for individual users, which is very convenient for self-management and various research purposes.

As described above, when the same user uses the physiological information recording device D again, since the processing unit 3 can discriminate that the user corresponds to the user information is already recorded in the biological information database 61, when the processing unit 3 writes the result of the test (that is, the physiological information of the user) into the storage unit 6, the connection relationship between the physiological information and the user is established. In other words, the processing unit 3 records the physiological information of the user in the storage unit 6 and causes the physiological information to correspond to the user information.

As described above, when a plurality of users use the physiological information recording device D of the present disclosure, the physiological information recording device D of the present disclosure can automatically identify the user using the physiological information recording device D according to some physiological characteristics of each user, and intelligently record changes in their physiological information. This function is especially suitable for rehabilitation or training processes, even if it is only used for daily weight record tracking and other functions, it can also play excellent results.

Referring to FIG. 1 to FIG. 4, in a preferred embodiment of the present disclosure, the physiological information recording device D further includes a drive unit 7 for driving the carrier board 1 to tilt or sway to one side accord to the control signal from the processing unit 3, thereby facilitating the application of the COP test method to evaluate the user's balance capability. Specifically, after the processing unit 3 drives the carrier board 1 to tilt or sway to one side by the drive unit 7, the processing unit 3 can determine the current position of the user's center of gravity (based on the outputs detected by the force transducers 111), and tilting or swaying of the carrier board (according to the control signal sent by the processing unit 3) to comprehensively evaluate the balance capability of the user U. Accordingly, the processing unit 3 determine the balance ability (balance index) of the user when tilting or swaying by the tilting or swaying of the carrier board and whether the user's center of gravity is offset to an area of feet standing (based on signals from multiple contact sensing elements 2). More specifically, the processing unit 3 records the center of gravity (COG) and the actual contact range at each time point, so that the two signals can be synchronously analyzed (e.g., the relationship between the center of gravity and the actual contact range at each time point, the change relationship between the center of the gravity and the actual contact range as time passes), and the analyzed result after the comprehensive judgment is obtained.

Principles and technical details of the COP test method are not described herein, and only a few practical problems encountered in the actual application are provided so that the advantages of the present disclosure can be understood easily. First of all, in a balance assessment, if only a COP displacement is known, it is difficult to represent the complete balance ability. For example, the COP displacement distance of standing on single leg must be less than the standing position of the two feet. It is impossible to judge from the data that the user's balance ability is good or not if the standing state (such as standing on one foot or standing on both feet) of the user at this time is not obtained at the same time. In addition, if COP sloshing occurs within the range of the span of the two feet, there is usually no doubt of falling, but if it is close to or exceeds the boundary of the span, there is a risk that the user will fall. Therefore, a complete assessment of the balance ability should be achieved by measuring both the change in the center of gravity and the position of the two feet. As can be seen from the foregoing description, since the physiological information recording device D of the present disclosure can accurately grasp the standing state of the user through the plurality of contact sensing elements 2 disposed on the surface of the carrier board 1, so that whether the user is standing alone or on both feet, or the feet are close together or not, can be faithfully reflected in the information collected by the processing unit 3, thus effectively avoiding the bias in the assessment of balance ability. Accordingly, the physiological information recording device D of the present disclosure is not only capable of coping with daily use of a general household (because of low cost), but also can be applied to reconstruction and various balance and dynamic training (because of high precision), and its application level is very wide.

In the embodiment of the present disclosure, when the processing unit 3 determines that the user's center of gravity has deviated to a critical point close to an effective support area of the two feet (such as within a certain distance of the boundary of the area) according to the received various signals, the physiological information recording device D of the present disclosure can generate a warning signal to prevent the user from falling during the test. Specifically, the foregoing warning signal may be driven by the display unit 3 to display a warning indicator, or an audio device such as a buzzer may be added to the physiological information recording device D (not shown). The processing unit 3 drives the audio device to emit a warning sound, or the processing unit 3 can also drive an illumination unit (not shown) as a warning light to emit light. As mentioned above, since a conventional device cannot accurately detect a force-bearing position, and cannot estimate the effective support area of the two feet according to the exact position of the user U's feet. Therefore, the conventional device does not achieve the effect of early warning, which may cause user U to face the risk of falling during the test.

In addition, when the embodiment of the present disclosure is used together with a feedback-type interactive rehabilitation system, the difficulty of controlling an interactive program of the interactive rehabilitation system can be controlled by individualized feedback according to the relationship of distance between the COG of the user U and the critical point of the support area. For example, when the calculated COG of the user U shows that the center of gravity of the user U falls within the safe area, the processing unit 3 can drive the carrier board 1 to perform a large amplitude shaking through the drive unit 7. Conversely, after tilting or swaying to one side, when the user U's COG shows that the user's center of gravity is very close to the critical point of the support area, the processing unit 3 drives the carrier board 1 in a gentle manner through the drive unit 7 to avoid accidents during the process under the test.

Second Embodiment

Figure 5:
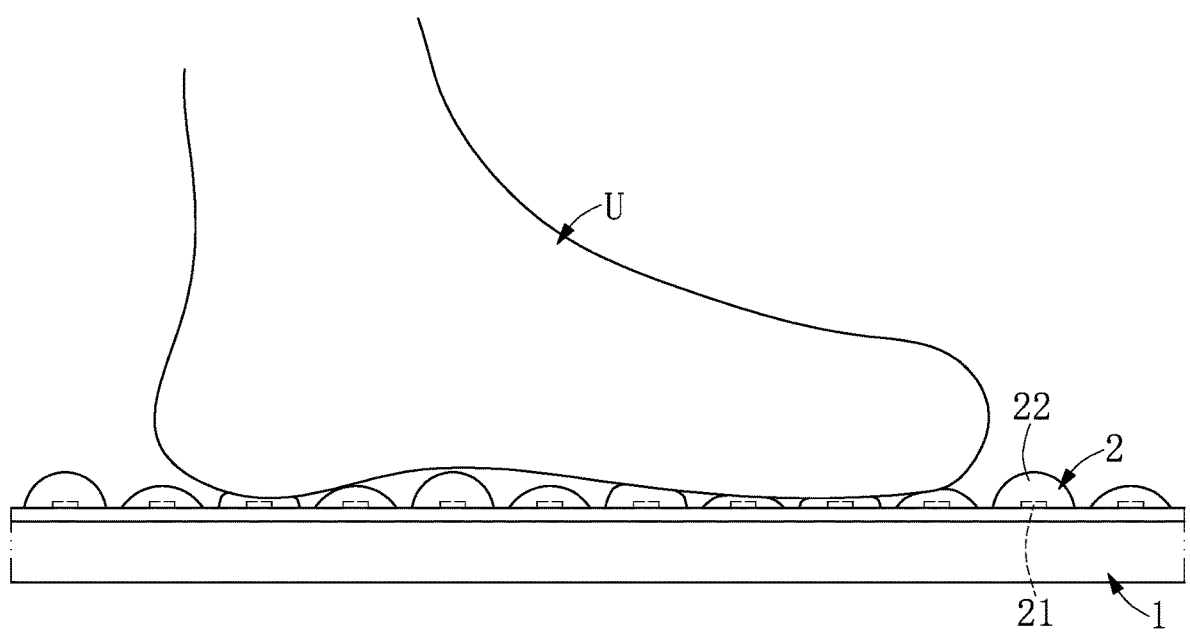
FIG. 5 is a side schematic view of a physiological information recording device according to a second embodiment of the present disclosure.

Referring to FIG. 5, and with reference to the symbol of each component shown in FIG. 1 and FIG. 2, FIG. 5 is a side schematic view of a physiological information recording device according to a second embodiment of the present disclosure. In the second embodiment of the present disclosure, the surface of the carrier board 1 of the present disclosure is provided with a plurality of bumps 22 which are made of a material having elasticity, and the bumps 22 are staggered on the surface of the carrier board 1. Each contact sensing element 2 is composed of the bumps 22 and the force-sensing resistors 21 disposed in the respective bumps 22. When the respective bumps 22 are pressed by an external force, the corresponding force-sensing resistor 21 is triggered, and then the contact sensing element 2 sends a signal to the processing unit 3. An advantage of such design is that the information received by the contact sensing element 2 can further reflect a height of the arch of a user U by the bumps 22 arranged in staggered high and low, which is beneficial to further understand and intelligently distinguishing the physiological characteristics of the user U. Specifically, for the user U with a higher arch, standing in the physiological information recording device D of the present disclosure will only cause the contact sensing element 2 in the higher bump 22 to be depressed and trigger the signal, and for the contact sensing element 2 in the lower bump 22, the signal will not be triggered. Conversely, for the user U with a flatter arch, the contact sensing element 2 will be depressed and trigger the signal regardless of the height of the bump 22. Accordingly, since the physiological information recording device D of the present disclosure can also detect the shape of the user U's arch, it is possible to obtain body information such as whether the user U has a flatfoot and a shape of the user's sole.

It should be noted that the bumps 22 may be formed on the surface of the carrier board 1 respectively, or may be an entire elastic film layer covering the surface of the carrier board 1, and a protrusion structure is formed at a position corresponding to each force-sensing resistor 21. The present embodiment is not limited thereto.

Third Embodiment

Figure 6:
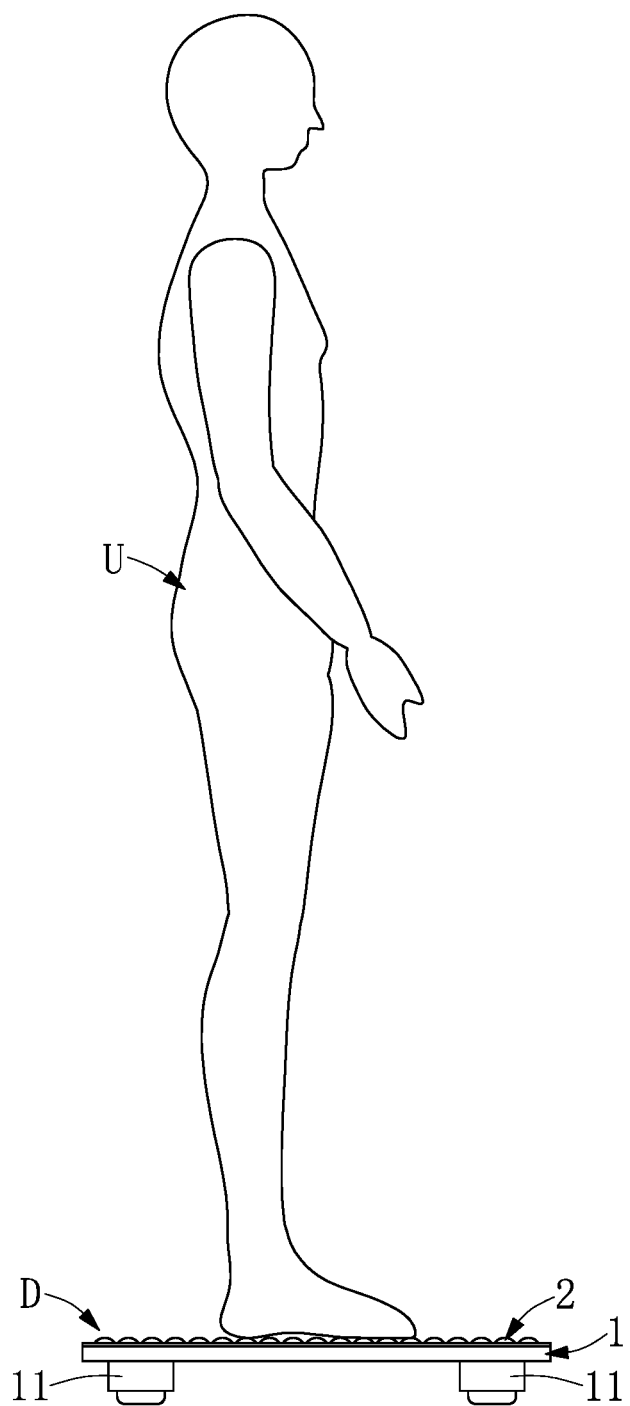
FIG. 6 is a schematic view of an initial standing state of the user performing squat on the physiological information recording device of the present disclosure.
Figure 7:
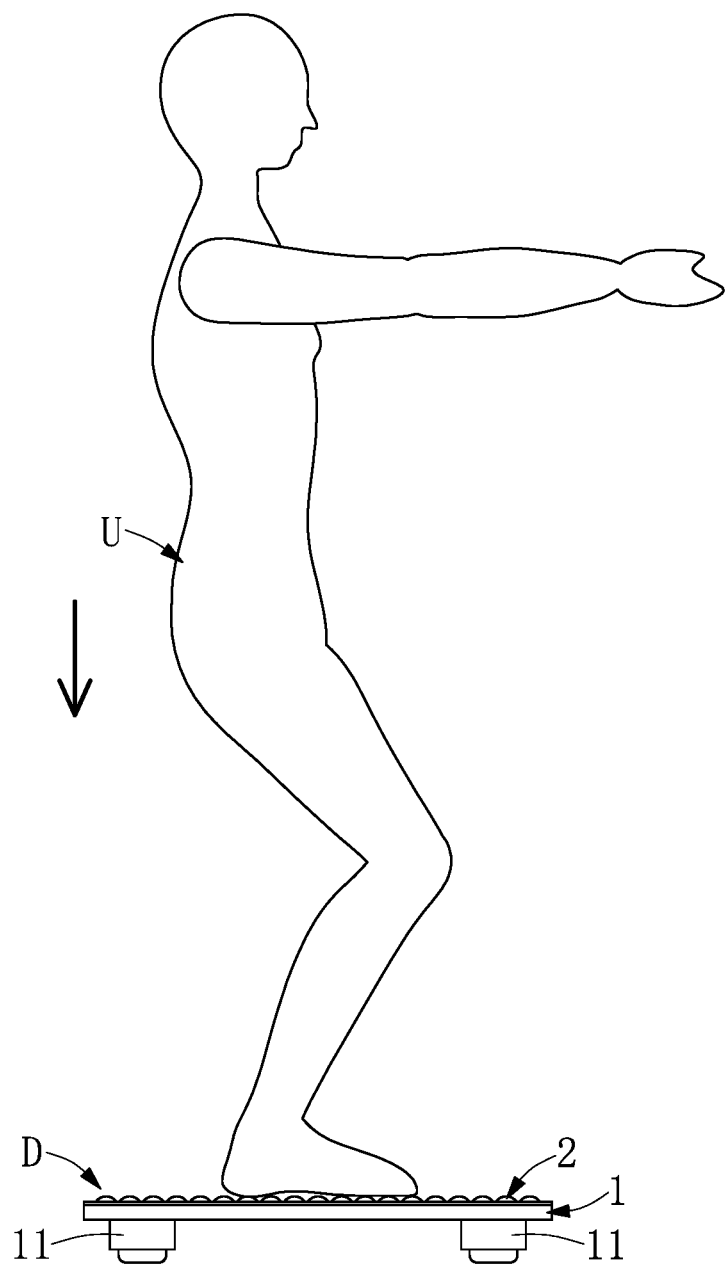
FIG. 7 is a schematic view of a centrifugation state of the user performing squat on the physiological information recording device of the present disclosure.
Figure 8:
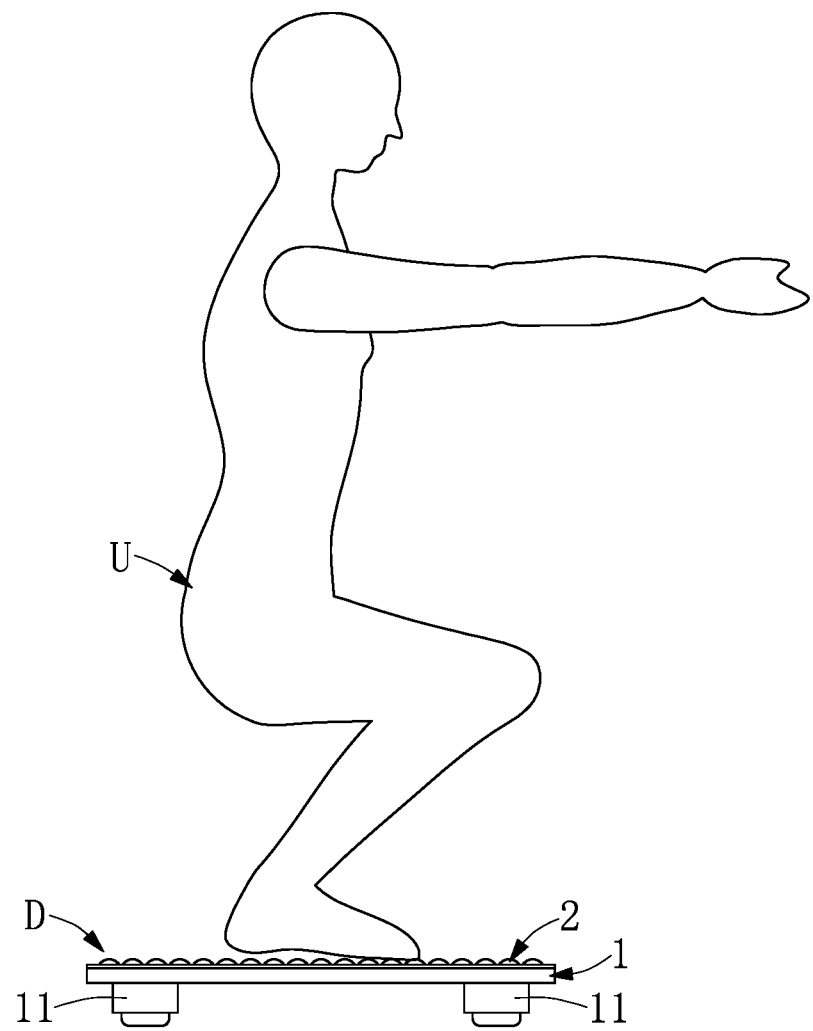
FIG. 8 is a schematic view of a squatting state of the user performing squat on the physiological information recording device of the present disclosure.
Figure 9:
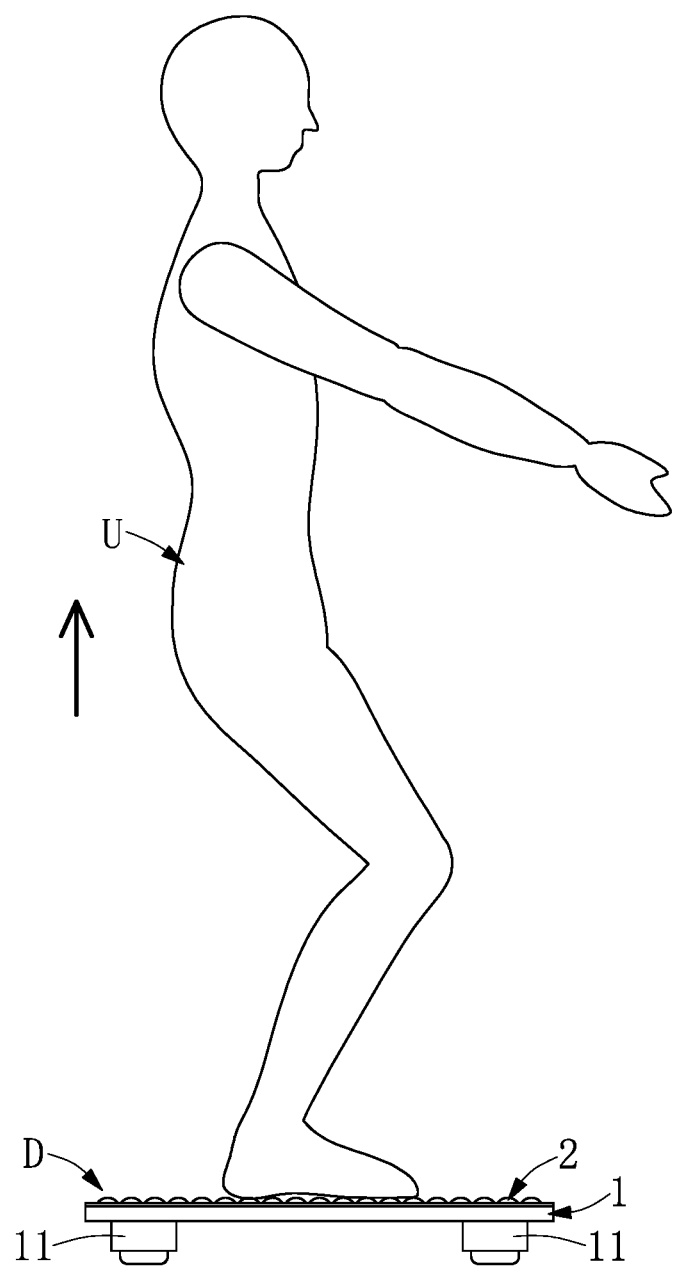
FIG. 9 is a schematic view of a centripetal of the user performing squat on the physiological information recording device of the present disclosure.
Figure 10:
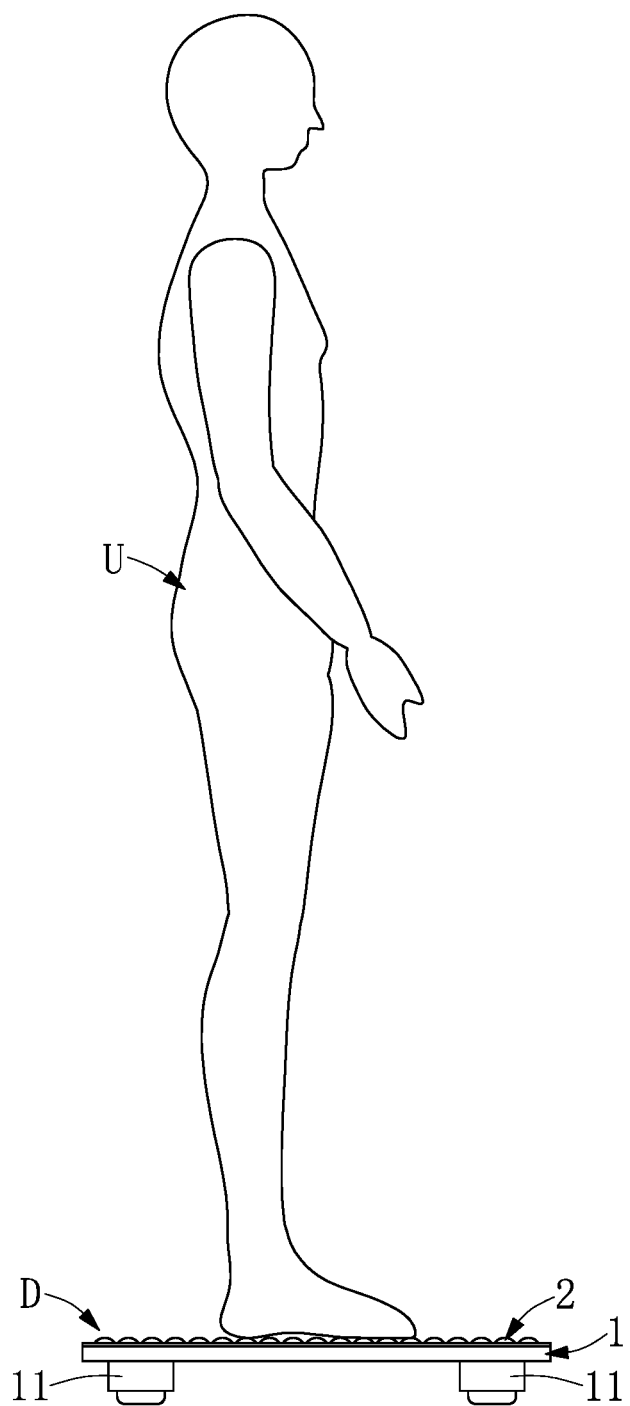
FIG. 10 is a schematic view of a recovery to a standing state of the user performing squat on the physiological information recording device of the present disclosure.

Referring to FIG. 6 to FIG. 10, and with reference to the symbol of each component shown in FIG. 1 and FIG. 2, FIG. 6 is a schematic view of an initial standing state of the user performing squat on the physiological information recording device of the present disclosure; FIG. 7 is a schematic view of a centrifugation state of the user performing squat on the physiological information recording device of the present disclosure; FIG. 8 is a schematic view of a squatting state of the user performing squat on the physiological information recording device of the present disclosure; FIG. 9 is a schematic view of a centripetal s of the user performing squat on the physiological information recording device of the present disclosure; and FIG. 10 is a schematic view of a recovery to a standing state of the user performing squat on the physiological information recording device of the present disclosure.

As can be seen from the above FIG.s, the physiological information recording device D of the present disclosure can also be applied to record and evaluate ability of the user U to perform various dynamic activities. In the present embodiment, the ability of the user U toe tipping has been mentioned firstly and can be recorded and evaluated by the physiological information recording device D of the present disclosure. In the foregoing application example, the change of the contact area and the weight are mainly combined to determine the number of cycles of toe tipping. However, the physiological information recording device D of the present disclosure is not limited to these applications. For further explanation, other application modes are described herein by squatting. However, the physiological information recording device D of the present disclosure is not limited thereto, and the examples given here are merely for the purpose of understanding the effects thereof, and are not intended to limit the field of application of the physiological information recording device D of the present disclosure.

Specifically, when the user U performs dynamic operations such as squatting, the weight of the carrier board 1 changes and a number of times the user U is squatted can be recorded by recording these weight changes. Although there during the squatting there is no change in the contact area of the sole like the toe tipping, the weight change will be very noticeable. In other words, the contact area and position of the two feet are stable and unchanged, but the weight changes significantly and periodically, and the user U's squat ability can be known. More specifically, in the eccentric contraction phase (as shown in FIGS. 6 to 8, that is, the process of user squatting), the weight of the carrier board 1 will suddenly become lighter, then suddenly rises before the user stops, and stabilizes at rest; on the contrary, in the concentric contraction phase (as shown in FIG. 8 to FIG. 10, that is, the process of user standing), since the user must step on the carrier board 1 to force the body to be propped up, the weight of the carrier board 1 will become heavier, fall at the user's standing timing, and then stabilize again in a stationary state. The processing unit 3 synchronously analyzes the position of center of gravity and the actual contact range, and may determine that the user U is in a centrifugal phase or a centripetal phase, and accordingly generates an analyzed result, and records the analyzed results to know the motion cycle of the user U. Recording the aforementioned cycle can understand the squatting process of the user U, and if the user performs an action that exceeds the capacity load, causing a pace to be unstable and stepping on different positions on the carrier board 1, these details which are valuable indicators for subsequent assessment of physical ability can also be accurately recorded.

Regardless of the aforementioned squats, or the activities of the toe tipping mentioned in the previous section, in practical applications, the number of times the user U is required to squat or tip toe can be preset, and when the user U completes the preset number of times, a set training target is completed. Therefore the present disclosure can be applied to a specific training item. On the other hand, the user U can squat or tip toe repeatedly without setting the target number, and the maximum number of times the user U can perform is recorded. In this way, in long-term tracking, changes in a physiological state of user U, which is very useful in rehabilitation therapy, can be understood.

In conclusion, one of the beneficial effects of the present disclosure is that, by the technical features of "the carrier board 1 provided with a plurality of force transducers 111, and the plurality of force transducers 111 defining at least one plane" and "the plurality of contact sensing elements 2 disposed on the surface of the carrier board 1" not only the function of multi-function detection at low cost can be achieved, but also further automatic identification, judgment, record and suggestion services can be intelligently provided.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A device for recording physiological information, the device comprising:
   a carrier board comprising a plurality of force transducers and a plurality of contact sensing elements, wherein all of the contact sensing elements are substantially, completely and evenly disposed on a top surface of the carrier board; and
   a processing unit, coupled to the force transducers and the contact sensing elements, configured to determine a center of gravity according to outputs of the force transducers, configured to determine a contacted range according to outputs of the plurality of contact sensing elements, and configured to record the center of gravity and the contacted range, wherein the contact range comprises a contact position and a contact area in the carrier board, and wherein the center of gravity and the contacted range substantially correspond to a same time point.

2. The device of claim 1, wherein the processing unit synchronously analyzes the center of gravity and the contacted range to produce an output result.

3. The device of claim 2, wherein the output result comprises a phase of squatting being in an eccentric contraction phase or a concentric contraction phase.

4. The device of claim 2, wherein the output result comprises a number of times of tiptoe.

5. The device of claim 1, wherein at least part of the contact sensing elements are bumps staggered with high and low to measure a shape of foot, wherein the shape of foot comprises a contour of foot and a height of arch of foot.

6. The device of claim 1, further comprising:
   a drive unit, coupled to the processing unit, configured to tilt or/and sway the carrier board according to a control signal from the processing unit;
   wherein the processing unit determines a balance index according to the center of gravity and the control signal when the carrier board is tilted or/and swayed.

7. The device of claim 1, wherein the processing unit generates a shape of foot according to the outputs of the plurality of contact sensing elements.

8. The device of claim 7, wherein the shape of foot comprises a contour of foot and a height of arch, wherein the processing unit identifies a user using the device according to the shape of foot.

9. The device of claim 1, wherein the contact sensing elements are low-resolution contact sensing elements.

10. The device of claim 1, wherein, the processing unit determines a center of pressure according to the outputs of the contact sensing elements, and analyzes the center of pressure and the center of gravity.

11. A method applied to a physiological information recording device that includes a carrier board comprising a plurality of force transducers and a plurality of contact sensing elements, wherein all of the contact sensing elements are substantially, completely and evenly disposed on a top surface of the carrier board, and a processing unit, and the method comprising:
   receiving outputs of the force transducers and outputs of the contact sensing elements;

determining, by the processing unit, a center of gravity according to the outputs of the force transducers;

determining, by the processing unit, a contacted range according to the outputs of the contact sensing elements, wherein the contact range comprises a contact position and a contact area in the carrier board; and recording, by the processing unit, the center of gravity and the contacted range, wherein the center of gravity and the contacted range substantially correspond to a same time point.

12. The method of claim 11, further comprising:
synchronously analyzing, by the processing unit, the center of gravity and the contacted range to produce an analyzed result.

13. The method of claim 12, wherein the output result comprises a phase of squatting being in an eccentric contraction phase or a concentric contraction phase.

14. The method of claim 12, wherein the output result comprises a number of times of tiptoe.

15. The method of claim 12, wherein at least part of the contact sensing elements are bumps staggered with high and low to measure the shape of foot, wherein the shape of the foot comprises a contour of foot and a height of arch of foot.

16. The method of claim 11, further comprising:
tilting or swaying the carrier board according to a control signal of the processing unit; and
determining a balance index according to the center of gravity and the control signal when the carrier board is tilted or swayed.

17. The method of claim 11, further comprising:
generating, by the processing unit, a shape of foot according to the outputs of the plurality of contact sensing elements.

18. The method of claim 17, further comprising:
identifying, by the processing unit, a user using the device according to the shape of foot.

19. The method of claim 17, wherein the shape of foot comprises a contour of foot and a height of arch.

* * * * *